United States Patent [19]

Land et al.

[11] Patent Number: 4,669,753
[45] Date of Patent: Jun. 2, 1987

[54] FINGERPRINT RECORD SYSTEM AND APPARATUS FOR AND METHOD OF RECORDING FINGERPRINTS

[76] Inventors: Larry D. Land, 1946 Edgerton, St. Paul, Minn. 55117; Gary J. Wallin, 14774 56th St. N., Stillwater, Minn. 55082

[21] Appl. No.: 850,019

[22] Filed: Apr. 10, 1986

[51] Int. Cl.⁴ .................... B42D 15/00; B41K 1/00; A61F 13/00

[52] U.S. Cl. .................... 283/1 A; 283/28; 283/68; 283/69; 283/70; 118/31.5; 428/40

[58] Field of Search ............. 283/1 A, 1 R, 28, 68, 283/69, 70; 118/31.5, 40; 427/1; 428/40, 48, 29

[56] References Cited

U.S. PATENT DOCUMENTS

| | | | |
|---|---|---|---|
| 2,020,376 | 11/1935 | Rich | 283/68 |
| 3,549,253 | 12/1970 | Brodie | 118/31.5 |
| 3,664,910 | 5/1972 | Hollie | 283/69 |
| 4,512,595 | 4/1985 | Breen | 283/70 |
| 4,557,964 | 11/1985 | Magnotta | 428/40 |

Primary Examiner—Paul A. Bell
Assistant Examiner—Paul M. Heyrana, Sr.
Attorney, Agent, or Firm—Warren A. Sturm

[57] ABSTRACT

A fingerprint, and the like, image-data records keeping system and apparatus provides for image-data review from each side of a transparent carrier base to allow an X-ray type of examination as by viewing an image-data record from the front and back. A method and apparatus for obtaining individual image-data records includes a soft, resilient working surface having low friction surface and a flexible base material coated with adhesive on one side for placement on the portion of a body of which fingerprints, or the like, are to be recorded.

7 Claims, 16 Drawing Figures

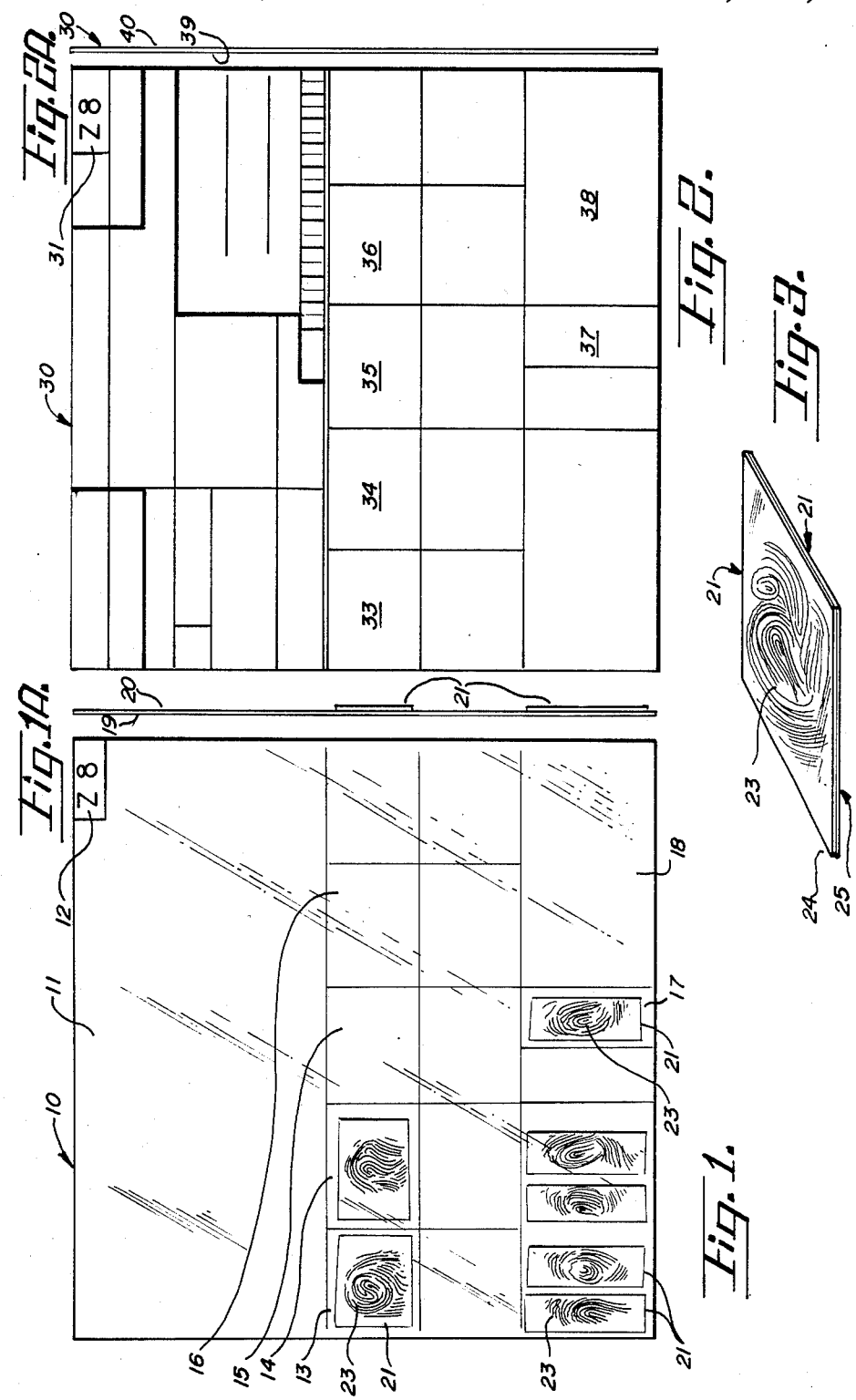

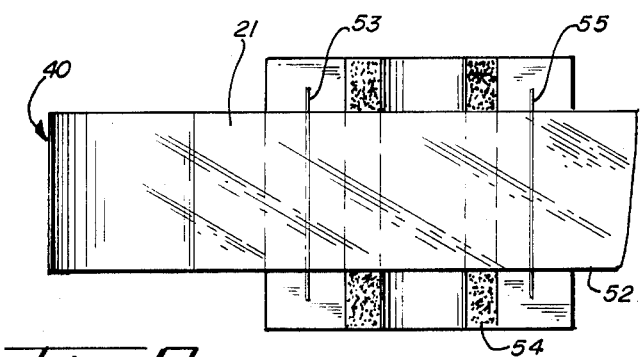
Fig. 8.
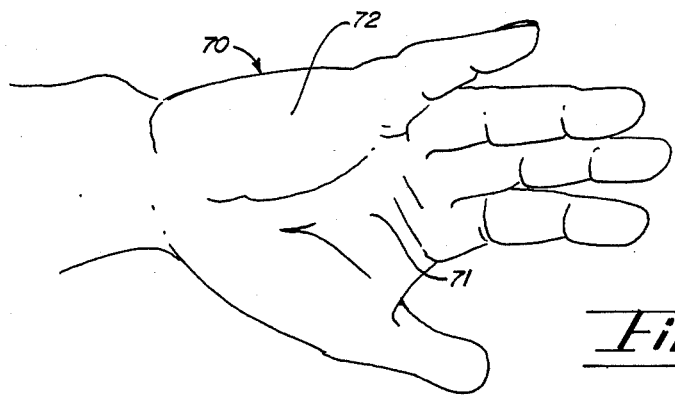
Fig. 9.
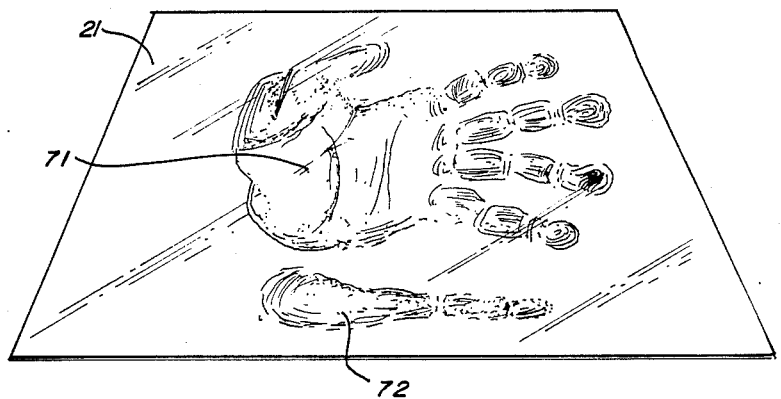

FINGERPRINT RECORD SYSTEM AND APPARATUS FOR AND METHOD OF RECORDING FINGERPRINTS

FIELD OF THE INVENTION

1. Background of the Invention

This invention relates generally the field of obtaining and recording fingerprint data and it is more particularly directed toward a records system and an apparatus for and method of recording fingerprints. Our invention is directed to a facile method and apparatus for obtaining accurate fingerprint records, to provide uniformity of such records and to facilitate retention, storage, and further processing of such records.

2. Prior Art

The following Patents were noted in a search of the prior art considered relevant to the field of our invention;

| Patent No. | Patentee | Patent Date |
|---|---|---|
| 2,313,807 | G. P. Curry | 2/03/1941 |
| 3,467,055 | J. Yonchar | 9/16/1969 |
| 3,479,987 | W. K. French | 11/25/1969 |
| 3,664,910 | M. E. Hollie | 5/23/1972 |
| 3,694,240 | M. Miller et al | 9/26/1972 |

The sum total of the above noted references may be an awareness that there are various and sundry records systems, identification systems and methods and apparatuses for obtaining records of fingerprints of an individual and thereafter processing the record, obtained and preserved, to provide for classification and comparison where desired.

The development of our invention has been occasioned by a deficiency perceived in present day and prior art methods and apparatus used by, for example, law enforcement organizations utilizing the unique characteristics of the ridges and valleys present on the hands and fingers of individuals that may, when properly used, serve as a complete and accurate identification of that individual. As one example of a difficulty existing with many present day procedures, printer's ink is rolled out on a piece of glass or other hard surface, the fingers and/or hand of an individual are pressed upon the film of printer's ink and the hand or fingers are then placed upon a clean sheet of, for example, paper and an impression is made to form a record. When this system is utilized, many of the records are then forwarded to a central location for recording and processing as by classification and the like.

Unfortunately, the method and apparatus utilized for obtaining the initial impression to form the print records, result in smudges or incomplete transfer of the impressions of the hand and finger characteristics so that the records have proven to be unusable and will have to be redone if the individual is available for such purposes. Another problem which has existed in recording the fingerprint data on a paper base is that many times it is desirable to look at a reverse impression of a fingerprint so that one may be looking toward the finger as is reflected by the print record and one may look at the record from the reverse side so that one is, in effect, looking through a finger to the pattern of the finger, as, for example, in an X-ray view. This is not possible with known present day systems, apparatus or methods of recording and preserving print records.

SUMMARY OF THE INVENTION

One general object of our invention is to provide a fingerprint records keeping system in which the records, or images, of finger and/or hand print of an individual are permanently retained on a transparent carrier which permits of suitable identification indicia and which may be displayed over an opaque carrier containing additional identification indica and in which the transparent carrier may be viewed from the front or the back as an X-ray film, as circumstance may require for the use of the recorded print data.

Another object of our invention is to provide a method and apparatus for obtaining the fingerprint records of an individual that is efficient, easy to utilize and which provides fingerprint records and data that may be displayed and recorded within our records keeping system.

Briefly, our records keeping system utilizes a thick transparent carrier and fingerprint records that have been provided upon a thin flexible transparent plastic base having an adhesive coating on the side on which the finger print impression is produced. The individual bases are then placed on predetermined locations on the rear surface on the transparent carrier adjacent to suitable indicia indentifying the nature of the print record and the adhesive retains the base upon the transparent base and the fingerprint records, or images may then be viewed from the front or the back of the transparent carrier. A second, opaque card is typically fastened to the transparent carrier so that indicia on the opaque card may be viewed thru the transparent carrier and the print records to provide further identification information or other data relative the fingerprints disposed upon and permanently mounted on the transparent carrier.

Our method of obtaining fingerprint records, or images, includes the steps of providing a suitably sized piece of thin flexible plastic material, preferably transparent, that is coated on one side with a suitable adhesive. The adhesive coated side is disposed upon or underneath the portion of a hand, such as a finger tip of an individual, first having coated the portion of the hand to be recorded with a suitable material, such as printer's ink, and then placing the fingertip or portion of the individual's hand over a resilient base such as foamed rubber or plastic, and while the adhesive on the surface on the plastic material retains the plastic in contact and at the desired location on the portion of the hand to be recorded, pressing down upon the hand over the foam base so that the plastic material is caused to conform to the surface of the individual's hand, without slipping, to transfer the surface irregularities on, for example, the fingertips of the individual to the adhesive disposed on the plastic surface of the flexible plastic material.

One example of an apparatus for accomplishing our improved method of recording the fingerprint images provides a flat top surface having a foamed resilient portion for receiving the fingertip of an individual and includes a roll of plastic tape, having the adhesive side disposed upwardly, that may be drawn over the top surface of the apparatus and a knife blade extending upwardly above the surface so that when the individual presses down on the top surface of the tape and the foamed plastic surface of the apparatus, the image of a fingerprint is recorded on the tape and the tape is severed from the supply roll simultaneously and after the desired engagement of the lower surface of the tape between the fingertip and the foam material, the tape will adhere to the tip of the finger of the individual and may thereafter be removed to a position on the transparent base carrier of our records keeping system.

Other objects and advantages of our invention may become apparent from a consideration of the appended specification claims and drawings in which:

FIG. 1 is a front view of a transparent carrier base for use with our invention;

FIG. 1A is a side view of the transparent base carrier shown in FIG. 1;

FIG. 2 is a front view of an opaque card to be used in connection with the transparent carrier base of FIG. 1;

FIG. 2A is a side view of the opaque card of FIG. 2;

FIG. 3 is a perspective sketch of a print record base for use in connection with the apparatus of FIGS. 1 & 2;

Figure 4A:
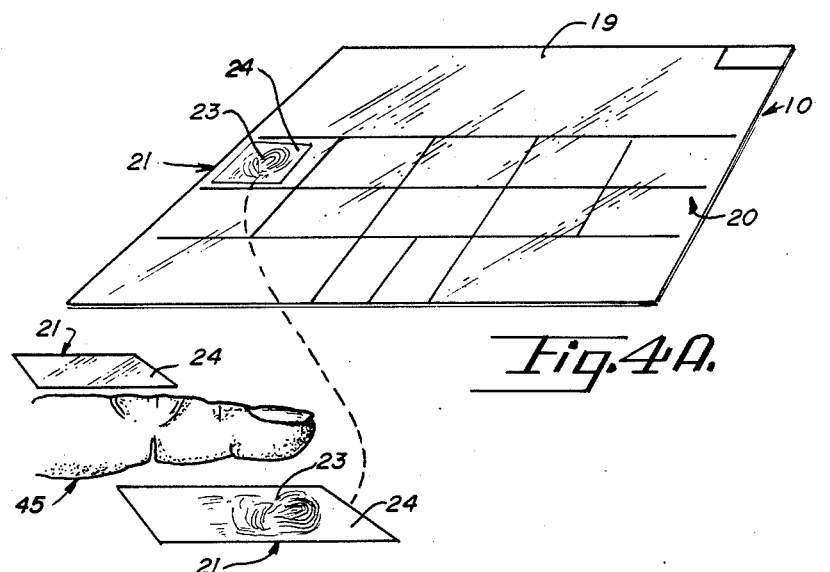
Figure 5:
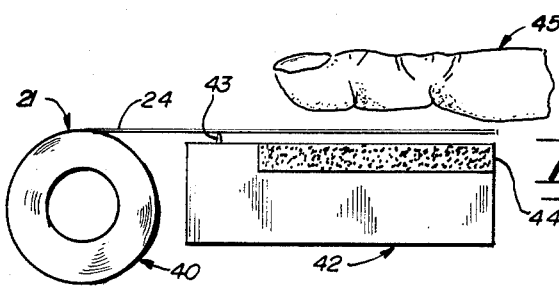
Figure 5A:
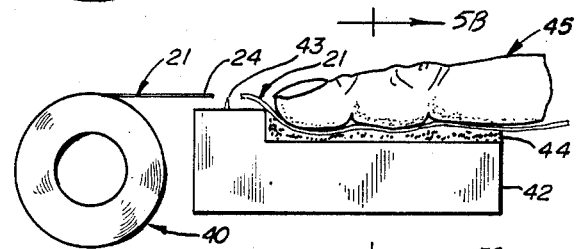
Figure 5B:
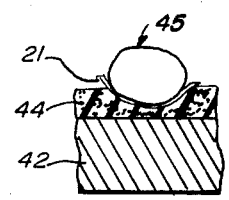
Figure 6:
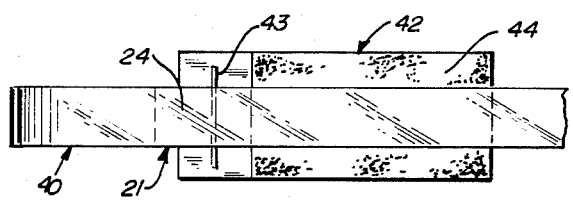
Figure 7:
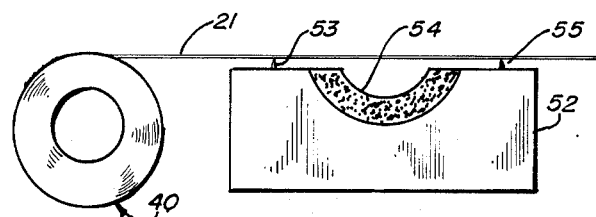
Figure 7A:
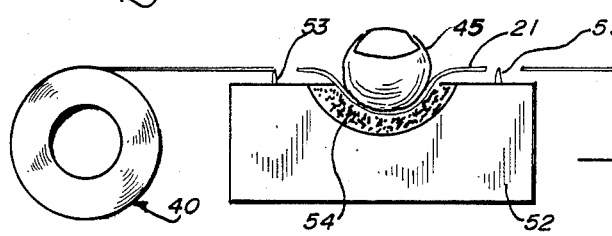

FIGS. 4A, B & C illustrate the several elements of FIGS. 1, 2, and 3 during intermediate and assembled states;

FIG. 5 is a side elevational view of a print recording apparatus;

FIG. 5A is a further side elevational view of a print recording apparatus;

FIG. 5B is fragmentary sectional view taken along section line 5B of FIG. 5A;

FIG. 6 is a top plan view of the apparatus shown in FIG. 5;

FIG. 7 is a side elevational view of another embodiment of apparatus for obtaining printed records of portions of an individual's hand;

FIG. 7A is a side elevational view of the apparatus shown in FIG. 7 with an individual finger in disposition as a print record is created;

FIG. 8 is a top plan view of the apparatus shown in FIG. 7; and

FIG. 9 is a side perspective view of a hand and tape for creating a full handprint record image.

DETAILED DESCRIPTION OF THE INVENTION

Referring now to the drawings in which like elements are identified by like reference characters, FIGS. 1 & 1A illustrate a front and side elevational view of a thick, flexible transparent record carrier base 10 having a plurality of fingerprint records disposed thereon.

Transparent base 10 is provided with space at the top, indicated by reference character 11, for receiving data that may be printed thereon and includes a code space 12 at the upper right hand corner looking toward the front of transparent base 10. Base 10 is also divided into a number of print record areas or spaces indicated by reference characters 13, 14, 15, 16, 17, and 18. The front side is indicated by reference character 19 and the rear, reverse side, is indicated by reference character 20.

Print records disposed on suitably sized tape segments 21 are shown affixed to the rear surface of transparent carrier base 10 and are held thereon by an adhesive layer 24 on the top of the tape segment 21.

Referring to FIG. 3, a tape segment, comprised of thin, transparent materials, 21 is shown having a top surface upon which is disposed a suitable adhesive layer 24, for the purpose for receiving and engaging a finger tip, or the like, of an individual to record a print, and for affixing the top surface of tape segment 21 to the rear surface of transparent carrier base 10, and a bottom surface 25.

FIGS. 2 and 2A illustrate a front and side elevational view of an opaque record card base 30 which is provided with a code number 31 at its upper right hand corner and areas adjacent to the top portion to permit recording of desired data and is similarly divided into a plurality of spaces (33, 34, 35, 36, 37, and 38) for positioning of print records, and includes a front surface 39 and a rear surface 40.

Figure 4B:
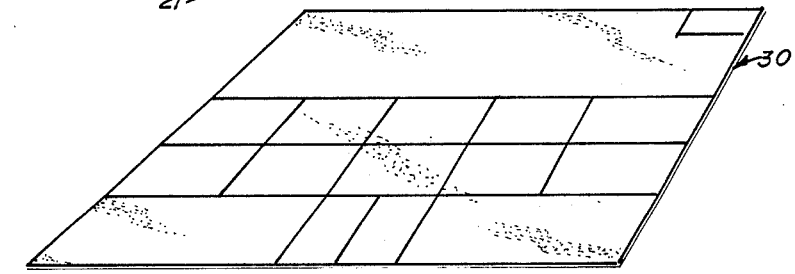
Figure 4C:
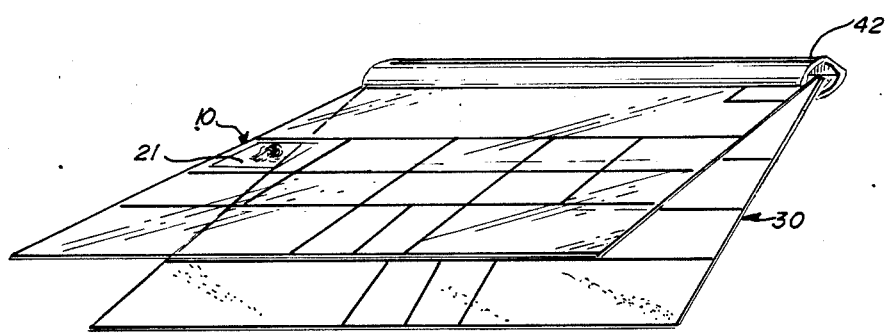

FIGS. 4A, 4B, and 4C illustrate the elements and a complete print record assemblage. In FIG. 4A, a transparent carrier base 10 is shown in position for receiving a plurality of print records, on tape segments 21, in the appropriate predetermined locations and adjacent the left end of FIG. 4A, a tape segment 21, having its top surface coated with a suitable adhesive. 24 is shown prior to and after the application of the finger tip from finger 45 to create a fingerprint record, or image 23, and the dotted line indicates the progression of the application of the adhesive coated upper surface of tape segment 21 to the rear surface of the transparent base 10. Record card 30 is shown disposed for receiving transparent carrier 10 in over laying registration and transparent base 10 and record card 30 ar shown affixed in such relationship in FIG. 4C by suitable binder, 42.

Transparent carrier base 10 may be comprised of relatively thick, suitable plastic material exhibiting transparency and stability under normal conditions of use as by handling by individuals responsible for processing the fingerprint and other data as may be carried thereon. Record card 30 may be comprised of suitable (preferably) opaque material such as paper and the like and exhibiting wear resistance and stability under conditions of normal use.

Tape 21 is perferably comprised of a relatively thin, flexible, stable material that may easily conform to the general irregular shape of the finger or hand of an individual as a print record is created and which may return to a flat planar disposition for a attachment to the rear surface of transparent carrier card 10. The adhesive material 24 preferably exhibits transparent characteristic while providing adequate adhesion to the rear surface of transparent carrier card 10 and which will engage the raised ridges on the surface of a finger or hand during the record creating process after which the temporary adhesion to the surface of the finger or hand is easily released for the permanent affixation to the rear surface of transparent base 10. One such suitable material is commercially available polyethene tape as sold under the brand name "Scotch" by the 3M Company of St. Paul, Minnesota.

FIGS. 5, 5A, 5B and 6 illustrate apparatus for performing the method of our invention for obtaining print records. A base 42 is provided with a generally planar upper surface with a portion of such surface being comprised of a layer of flexible, resilient material, such as foamed plastic or rubber. A sharp knife edge 43 is disposed transversely across the top surface for purposes to be explained below. A supply roll, 40, of suitable flexible, adhesive coated tape 21 is shown having its top surface and adhesive portion 24 exposed upwardly. Base 42 may be suitably configured for the attachment to the tape dispensing end of any one of the number commercially available tape dispensers.

FIGS. 7, 7A and 8 illustrate another form of apparatus for practicing our method of creating fingerprint, or the like, records and is shown having a base 52 with an upper surface containing a transversly extending semicircular slot that is lined with resilient foamed material 54 and a pair of transversly extending upwardly facing knife strips 53 and 55. A supply of tape 40 is adapted to provide a source of suitable tape 21 as described above.

FIG. 9 is illustrative of the creation of a print record of an entire hand and its side opposite the thumb. A left hand 70 is shown disposed and poised for the creation of a print record on the adhesive layer on the top surface of a large tape segment 21. Hand 70 is shown having a bottom surface 71 and a side surface 72. As the hand is placed on top of adhesive coating 24 on tape 21 with either the bottom or side surface on the adhesive coating, a print record is created of the side 72 and the bottom of 71 as illustrated in the sketch of the upper surface of the tape segment 21.

OPERATION

Referring to FIGS. 1, 2, 3 and 4, our records keeping system is shown comprised of transparent carrier base 10 having a plurality of recorded print images 23, disposed on the front or upper surface of tape segments, in predetermined locations and affixed to the rear surface of base 10 so as to be visible from the front and the rear for observation and perusal by others while maintained in a secure position between the lower surface of tape segments 21 and the rear surface of transparent base 10.

Transparent carrier base 10 may be utilized by itself, or as anticipated, as an overlay over a record card 30 that is provided with suitable areas for recording additional information and is divided into other suitable areas for registration with the materials recorded on the front surface of transparent card 10. Separable fastener 42 disposed across the top of transparent base 10 and card 30 may be removed and the two elements used separately and then re-assembled into registration for storage and retrieval. The method and apparatus illustrated in FIGS. 5 to 8 (inclusive) are similar in nature and as may be seen, when a finger 45, coated with suitable ink or powder, is disposed onto the adhesive 24 on the upper surface of tape 21 and the finger pressed downwardly into the foam portion 44 and 54 on bases 42 and 52, the tape 21 is cut by the knife blades and will adhere to and conform generally with the surface of finger 45 as finger 45 is depressed downwardly into the foamed, resilient material. The tape will be held in contact with the surface of the finger by the adhesive and may be slidably received on the upper surface of the foam so that as the tape conforms to the general shape of the portion of the finger of which a record is to be created, the raised portions of the surface will be transferred to the adhesive coating on the tape and regardless of motion of the finger, the tape will be maintained in its initial disposition, with respect to the surface and a clear impression may be obtained. The print record 23 contained on the portion segment 21, as severed by the knife blades 43 or 53 and 55, may then be applied, adhesive side forward, to the rear surface of a transparent carrier base 10. It may be noted that the foam material provides for engagement of the side portions of a finger or other irregular object without requiring rolling of the same or any other physical movement except a downward movement so that distortion of the surface irregularities is reduced to a minimum amount.

In FIG. 9, a tape segment 21, of suitable size, is provided to accept the entire bottom surface of a hand and a suitable print of the entire hand may be produced by placing tape 21 over a flexible resilient base (such as foamed plastic) to provide a print record. It may be noted that we have perceived that a record of the entire side portion a hand adjacent the little finger is desirable as a record for use in determining the identity of the individual from whom print records are obtained.

We claim:

1. A print records keeping system comprising in combination;
    a stable, transparent carrier base divided into discrete areas for displaying print and including identification indicia; and
    a plurality of print records, each comprising a flexible transparent base and having an adhesive coating on the front surface of thereof and a print image disposed on the adhesive coating and each attached to one of said discrete areas with the adhesive coating in engagement with the rear surface of said carrier base.

2. The subject matter of claim 1 and a record card including discrete areas for recording data and indicia to register with indicia disposed on the carrier base, said record card having the same dimensions as said carrier base and means attaching the top of said carrier base to the top of said record card where by the images of the prints on said carrier base may be readily viewed from the front or reverse side thereof.

3. The method of storing and preserving prints, comprising;
    providing a transparent carrier base;
    determining discrete areas for receiving print indicia;
    providing a flexible transparent tape including adhesive coating on the front surface thereof;
    recording a print image on the adhesive coating; and
    affixing the print image and tape by applying the adhesive coating to the rear surface of said transparent carrier base at one of said discrete areas.

4. Apparatus for recording print images comprising, in combination;
    a base having an upper surface;
    a volume of resilient formed material including an upper surface exhibiting low frictional characteristic disposed the top of the said base for receiving the surface of a flangial extremity of an individual;
    means for supplying a flexible transparent tape having adhesive coating on its top surface over said foamed portion of said base.

5. The subject matter of claim 4 in which the tape is disposed on a roll mounted adjacent the base and a cutting edge extends across the base intermediate said tape roll and the volume of resilient material whereby the application of body surface to be printed into said volume of resilient material effects severing of said tape.

6. The subject matter of claim 4 in which the upper surface of the volume of the resilient material is configured to accept the portion of the body of the individual from which a print image is desired.

7. The method of recording images of the surface configuration of portion of a body which comprises the steps of;
    providing a volume of resilient material having an upper surface exhibiting low friction characteristics;
    disposing transparent flexible material thereover, said material having an adhesive coating on its upper surface;
    placing the portion of the body of which a printed image is to be taken of the surface characteristics on the adhesive on said tape; and
    depressing said body portion onto said tape and into said resilient material.

* * * * *